United States Patent
Arifuku et al.

(10) Patent No.: US 11,884,641 B2
(45) Date of Patent: Jan. 30, 2024

(54) METHOD FOR DECOMPOSING FLAVONOID GLYCOSIDE AND METHOD FOR PRODUCING FLAVONOID

(71) Applicant: Showa Denko Materials Co., Ltd., Tokyo (JP)

(72) Inventors: Motohiro Arifuku, Tokyo (JP); Yoshiaki Kurihara, Tokyo (JP); Masato Kaneeda, Tokyo (JP)

(73) Assignee: RESONAC CORPORATION, Tokyo (JP)

( * ) Notice: Subject to any disclaimer, the term of this patent is extended or adjusted under 35 U.S.C. 154(b) by 0 days.

(21) Appl. No.: 17/263,141

(22) PCT Filed: Jul. 26, 2019

(86) PCT No.: PCT/JP2019/029526
§ 371 (c)(1),
(2) Date: Jan. 25, 2021

(87) PCT Pub. No.: WO2020/022508
PCT Pub. Date: Jan. 30, 2020

(65) Prior Publication Data
US 2021/0188796 A1    Jun. 24, 2021

(30) Foreign Application Priority Data
Jul. 27, 2018 (WO) .................. PCT/JP2018/028278

(51) Int. Cl.
*C07D 311/40* (2006.01)
*C07D 311/30* (2006.01)

(52) U.S. Cl.
CPC .......... *C07D 311/40* (2013.01); *C07D 311/30* (2013.01)

(58) Field of Classification Search
CPC .................................................. C07D 311/40
See application file for complete search history.

(56) References Cited

U.S. PATENT DOCUMENTS

2010/0191003 A1\*  7/2010  Isobe .................. C07D 309/32
549/403

FOREIGN PATENT DOCUMENTS

| CN | 101715445 | | 5/2010 |
|---|---|---|---|
| CN | 107501224 | | 12/2017 |
| JP | 2005145824 | | 6/2005 |
| JP | 2008208064 | | 9/2008 |
| JP | 2011-153084 | \* | 8/2011 |
| WO | 2008155890 | | 12/2008 |

OTHER PUBLICATIONS

Balu et al. (ChemSusChem 2012, 5, 1694-1697).\*
Puccini et al. (Chemical Engineering Transactions, 50, 223-228).\*
Nakagawa (J. Nat. Prod. 2006, 69, 1177-1179).\*
Secmeler et al. (Food Chemistry 265 (2018) 298-307).\*
Kim et al. (Separation Science and Technology, 44:2598-2608, 2009).\*
Matej Ravber, et al., "Optimization of hydrolysis of rutin in subcritical water using response surface methodology," The Journal of Supercritical Fluids, vol. 104, May 2015, pp. 145-152.
Duangkamol Ruen-Ngam, et al., "Hydrothermal Hydrolysis of Hesperidin Into More Valuable Compounds Under Supercritical Carbon Dioxide Condition," Industrial & Engineering Chemistry Research, vol. 51, Oct. 2012, pp. 13545-13551.
Mateja Germ, et al., "The temperature threshold for the transformation of rutin to quercetin in Tartary buckwheat dough," Food Chemistry, vol. 283, Jan. 2019, pp. 28-31.
Matej Ravber; et al., "Optimization of hydrolysis of rutin in subcritical water using response surface methodology," The Journal of Supercritical Fluids, vol. 104, Sep. 2015, pp. 145-152.
Duangkamol Ruen-Ngam; et al., "Hydrothermal Hydrolysis of Hesperidin Into More Valuable Compounds Under Supercritical Carbon Dioxide Condition," Industrial & Engineering Chemistry Research, vol. 54, Oct. 2012, pp. 13545-13551.

\* cited by examiner

*Primary Examiner* — Valerie Rodriguez-Garcia
(74) *Attorney, Agent, or Firm* — JCIPRNET

(57) ABSTRACT

Provided is a method for decomposing a flavonoid glycoside, wherein a flavonoid glycoside-containing raw material is hydrothermally treated to decompose a flavonoid glycoside into a flavonoid.

10 Claims, No Drawings

METHOD FOR DECOMPOSING FLAVONOID GLYCOSIDE AND METHOD FOR PRODUCING FLAVONOID

CROSS-REFERENCE TO RELATED APPLICATION

This application is a 371 application of the International PCT application serial no. PCT/JP2019/029526, filed on Jul. 26, 2019, which claims the priority benefit of International PCT application serial no. PCT/JP2018/028278, filed on Jul. 27, 2018. The entirety of each of the above-mentioned patent applications is hereby incorporated by reference herein and made a part of this specification.

TECHNICAL FIELD

The present invention relates to a method for decomposing flavonoid glycosides and a method for producing flavonoids.

BACKGROUND ART

Flavonoids are a group of naturally occurring organic compounds, and are contained in flowers, leaves, roots, stems, fruits, seeds and the like of various plants including citrus fruits and beans. Flavonoids have different characteristics and actions depending on the type, but most of them have a strong antioxidant action. For example, polymethoxyflavone, which is a flavonoid contained in citrus fruits, is known to have an antioxidant action, a carcinogenic inhibitory action, an antibacterial action, an antiviral action, an antiallergic action, a melanin production inhibitory action, a blood glucose level inhibitory action, and the like, and is expected to be applied to various applications such as pharmaceuticals, health foods, and cosmetics.

Regarding a method for producing flavonoids from citrus fruits, for example, a method for extracting flavonoids in an aqueous ethanol solution from the pericarp of citrus fruits and the like and collecting the extracted flavonoids from the solution is known (for example, refer to Patent Literature 1).

CITATION LIST

Patent Literature

[Patent Literature 1]
Japanese Patent Laid-Open No. 2005-145824

SUMMARY OF INVENTION

Technical Problem

However, the conventional method for producing flavonoids has a problem of the yield of flavonoids being low. Therefore, it is required to develop a production method through which it is possible to improve the yield of flavonoids.

For example, the pericarp of citrus fruits contains a larger amount of flavonoid glycosides than flavonoids, but if this can be collected as flavonoids, the yield of flavonoids can be improved. Examples of a method for decomposing flavonoid glycosides into flavonoids include a method for reacting flavonoid glycosides with an acid such as hydrochloric acid. However, this method has problems that a used acid may remain and be mixed into the product and a side reaction product of the acid and flavonoids may be produced. Examples of a method for removing impurities such as an acid and byproducts include a method for separating and purifying flavonoids in the decomposition product by liquid chromatography, but this method has problems of high cost and poor production efficiency. Therefore, there is a need for a new method for decomposing flavonoid glycosides, which does not use an acid.

The present invention has been made in view of the above problems in the related art, and an objective of the present invention is to provide a method for decomposing flavonoid glycosides through which it is possible to efficiently decompose flavonoid glycosides into flavonoids without using an acid and a method for producing flavonoids through which it is possible to improve the yield of flavonoids.

Solution to Problem

In order to achieve the above objective, the present invention provides a method for decomposing flavonoid glycosides in which a raw material containing flavonoid glycosides is performed a hydrothermal treatment to decompose the flavonoid glycosides into flavonoids.

According to the method, it is possible to efficiently decompose flavonoid glycosides into flavonoid by a hydrothermal treatment without using an acid. In addition, it is possible to efficiently produce flavonoids at low cost using this method.

In the method, the flavonoid glycosides may contain sudachitin glycosides and/or demethoxysudachitin glycosides. According to the method, sudachitin glycosides and demethoxysudachitin glycosides can be decomposed particularly efficiently.

In the method, the hydrothermal treatment temperature may be in a range of 110 to 300° C. When the temperature is within the above range, it is possible to further promote decomposition of the flavonoid glycosides.

The present invention also provides a method for producing flavonoids including a decomposition process in which flavonoid glycosides are decomposed by the method of the present invention and an extraction process in which flavonoids are extracted from a decomposition product obtained in the decomposition process. According to this production method, it is possible to produce flavonoids in a high yield, at low cost, and efficiently.

Advantageous Effects of Invention

According to the present invention, it is possible to provide a method for decomposing flavonoid glycosides through which it is possible to efficiently decompose flavonoid glycosides into flavonoids without using an acid and a method for producing flavonoids through which it is possible to improve the yield of flavonoids.

DESCRIPTION OF EMBODIMENTS

The present invention will be described below in detail with reference to preferable embodiments. However, the present invention is not limited to the following embodiments.

In this specification, when a numerical range is indicated using "to," it means that numerical values stated before and after "to" are included as a minimum value and a maximum value. In the numerical ranges described stepwise in this specification, an upper limit value or a lower limit value described in the numerical range in a certain step may be arbitrarily combined with an upper limit value or a lower limit value described in the numerical range in another step. In the numerical ranges described in this specification, the upper limit value or the lower limit value of the numerical range may be replaced with values shown in examples. The term "A or B" may include either or both of A and B. Unless otherwise specified, materials exemplified in this specification may be used alone or two or more thereof may be used in combination.

(Method for Decomposing Flavonoid Glycosides)

A method for decomposing flavonoid glycosides according to the present embodiment is a method for decomposing flavonoid glycosides into flavonoids by performing a hydrothermal treatment on a raw material containing flavonoid glycosides.

Flavonoid glycosides are hydrophilic compounds having a structure in which flavonoids and sugars are linked by glycoside bonds. Flavonoids (aglycones), which are a source of flavonoid glycosides, are aromatic compounds having a phenylchromane framework as a basic structure, and examples thereof include flavones, flavonols, flavanones, flavanonols, isoflavones, anthocyanins, flavanols, chalcones, and aurones. Among these, the flavonoid may be polymethoxyflavone, which is a flavone.

Examples of polymethoxyflavones include sudachitin, demethoxysudachitin, nobiletin, tangeretin, pentamethoxyflavone, tetramethoxyflavone, and heptamethoxyflavone. Among these, the polymethoxyflavone may be sudachitin or demethoxysudachitin.

In addition, flavonoids may include quercetin, hesperetin, or anthocyanidin.

Sugars that are a source of flavonoid glycosides are not particularly limited, and examples thereof include known sugars that may be linked to the above flavonoids by glycoside bonds to form glycosides.

The raw material to be subjected to the hydrothermal treatment may contain components other than flavonoid glycosides. Examples of other components include flavonoids, water-soluble dietary fibers, slowly soluble dietary fibers, and sugars. The content of the flavonoid glycosides in the raw material with respect to a total amount of the solid content in the raw material is preferably 0.1 mass % or more, more preferably 0.25 to 30 mass %, still more preferably 0.3 to 15 mass %, and particularly preferably 0.5 to 5 mass %. When the raw material further contains flavonoids, the content of the flavonoid glycosides with respect to 1 part by mass of the content of the flavonoids is preferably 0.25 parts by mass or more, more preferably 0.5 to 100 parts by mass, and still more preferably 5 to 50 parts by mass.

Specifically, flowers, leaves, roots, stems, fruits, seeds, and the like of plants and seaweeds may be used as raw materials. In particular, since the pericarp contains a large amount of polymethoxyflavone and their glycosides, the squeezed residue of citrus fruits may be preferably used. In addition, the raw material may be a dry powder obtained from citrus fruits or a dry powder obtained from the pericarp of citrus fruits. Examples of citrus fruits include *Citrus sudachi*, *Citrus unshiu*, *Citrus poonensis*, and *Citrus depressa*. The citrus fruits may be *Citrus sudachi* containing a large amount of polymethoxyflavones such as sudachitin and demethoxysudachitin, and their glycosides.

The hydrothermal treatment may be performed by putting the raw material into a pressure-resistant sealed container together with water, and performing heating at a temperature of higher than 100° C. in the sealed state. When a reaction solution containing the raw material and water is heated in the sealed container, the inside of the sealed container has a heated and pressurized environment, and the hydrothermal treatment (hydrothermal synthesis) is performed.

The hydrothermal treatment may be performed by supplying water vapor (steam) into the sealed container from the outside. When water vapor is supplied from the outside, the temperature and pressure of the inside of the sealed container may be raised in a short time, and the hydrothermal treatment environment can be easily formed and maintained. Water vapor can be supplied using, for example, a boiler. Supply of water vapor may be performed in combination with a method for heating a reaction solution containing the raw material and water in a sealed container. The amount of water vapor supplied is appropriately adjusted so that the inside of the sealed container has a predetermined temperature and pressure.

The hydrothermal treatment may be performed while stirring the reaction solution. Regarding the pressure-resistant sealed container, known containers that can be used for the hydrothermal treatment can be used without particular limitation. Regarding the pressure-resistant sealed container, for example, an autoclave can be used.

The amount of water is not particularly limited as long as it is an amount sufficient for performing the hydrothermal treatment, and the solid content of the raw material with respect to 100 parts by mass of water may be 1 part by mass or more, 2 parts by mass or more, 4 parts by mass or more, or 5 mass or more and may be 100 parts by mass or less, 33 parts by mass or less, 25 parts by mass or less, 18 parts by mass or less, or 11 parts by mass or less. In addition, the content of the solid content of the raw material in the reaction solution (concentration of the raw material) with respect to a total amount of the reaction solution may be 1.0 mass % or more, 2.0 mass % or more, 3.8 mass % or more, or 4.8 mass % or more and may be 50 mass % or less, 25 mass % or less, 20 mass % or less, 15 mass % or less, or 10 mass % or less. When the amount of water or the concentration of the raw material is within the above range, it is possible to efficiently decompose flavonoid glycosides. In addition, if the ratio of the solid content of the raw material with respect to water or the concentration of the raw material is equal to or less than the upper limit value, the yield of flavonoids tends to improve when flavonoids are extracted from a decomposition product obtained by the decomposition method of the present embodiment.

The reaction solution containing the raw material and water may contain a solvent other than water or may contain only water as a solvent. The content of water in the solvent with respect to a total amount of the solvent may be 50 to 100 mass %, 70 to 100 mass %, 90 to 100 mass %, or 95 to 100 mass %. When the content of water in the solvent is equal to or larger than the lower limit value, since the solubility of flavonoid glycosides in the solvent can increase, it is possible to further promote decomposition of the flavonoid glycosides.

The reaction solution preferably does not contain an acid. In particular, the reaction solution preferably does not contain an inorganic acid such as hydrochloric acid, sulfuric acid, and nitric acid. When the reaction solution contains an inorganic acid, this is not preferable because highly toxic organochlorine compounds, organic nitrogen-based compounds, and organic sulfur-based compounds are easily produced by the hydrothermal treatment in the sealed container. In addition, when the reaction solution contains an inorganic acid, there is a risk of the acid remaining in the product and there is also a problem of high cost because a process of sufficiently removing an inorganic acid is required to prevent the acid from remaining in the product.

The content of the inorganic acids in the reaction solution with respect to a total amount of the reaction solution is preferably 1 mass % or less, 0.1 mass % or less, or 0.01 mass % or less. Here, the incorporation of an organic acid derived from a living body such as citric acid, acetic acid, aspartic acid, amino acid, and nucleic acid is not particularly limited. In this specification, the total amount of the reaction solution means a total amount of the reaction solution before the hydrothermal treatment is performed (before heating and pressurizing are performed in the sealed container).

The content of flavonoid glycosides in the reaction solution with respect to a total amount of the reaction solution may be 0.005 mass % or more, 0.01 mass % or more, 0.02 mass % or more, or 0.03 mass % or more and may be 10 mass % or less, 5 mass % or less, 3 mass % or less, 1 mass % or less, 0.9 mass % or less, 0.5 mass % or less, 0.3 mass % or less, or 0.1 mass % or less. When the content is equal to or larger than the lower limit value, the flavonoid production efficiency tends to improve. On the other hand, when the content is equal to or less than the upper limit value, the yield of flavonoids tends to improve when flavonoids are extracted from a decomposition product obtained by the decomposition method of the present embodiment. This is thought to be caused by the fact that, if the concentration of flavonoid glycosides in the reaction solution is high, when sugars separated from the flavonoid glycosides are polymerized (caramelization reaction) and amino acids are present in the reaction solution, the sugars and the amino acids are easily polymerized (Maillard reaction). Polymers of sugars (caramelization reaction product and Maillard reaction product) are unlikely to be dissolve in water or an alcohol. Then, it is speculated that decomposed flavonoids are incorporated into the sugar polymers and extraction of flavonoids is hindered, which causes decrease in the yield of flavonoids.

Reaction conditions for the hydrothermal treatment are not particularly limited, and may be, for example, 110 to 300° C. for 0.5 to 20 hours. The reaction temperature is preferably 120 to 190° C., and more preferably 140 to 185° C. When the reaction temperature is 110° C. or higher, the hydrothermal reaction tends to occur more favorably, and when the reaction temperature is 300° C. or lower, the raw material and the flavonoid are unlikely to be carbonized, and the yield tends to be further improved. The reaction time is preferably 0.5 to 20 hours and more preferably 1 to 10 hours. When the reaction time is 0.5 hours or longer, the reaction is more likely to proceed, and when the reaction time is 20 hours or shorter, it is easier to achieve a balance between the progress of the reaction and the cost.

In order to improve the yield of flavonoids, the hydrothermal treatment is preferably performed under conditions of a low temperature (for example, lower than 200° C.) for a long time (for example, 1 hour or longer). When the reaction temperature is a high temperature, bumping of the reaction solution is likely to occur during cooling after the reaction, and the reaction solution scatters out of the container containing the reaction solution when bumping occurs, and thus the yield tends to decrease. In addition, when cooling is performed to prevent the occurrence of the above bumping, since a long cooling time is necessary, work efficiency decreases. This problem of long cooling time is a disadvantage particularly when a large amount of flavonoids is produced. In order to address such problems, the hydrothermal treatment is preferably performed under conditions of a low temperature for a long time. Even if the hydrothermal treatment is performed at a low temperature, sufficient flavonoid glycosides can be decomposed into flavonoids by prolonging the reaction time. In addition, when the hydrothermal treatment is performed under conditions of a low temperature for a long time, it is possible to shorten the entire process time including the cooling time after the hydrothermal treatment compared with when the hydrothermal treatment is performed under conditions of a high temperature for a short time.

The pressure in the container during the hydrothermal treatment may be a saturated vapor pressure corresponding to the reaction temperature or higher, but the saturated vapor pressure is preferable in consideration of pressure resistance of the device. When water vapor is supplied into the sealed container, it is preferable to supply saturated water vapor at the above reaction temperature. The pressure in the sealed container during the hydrothermal treatment can be, for example, 0.2 to 1.6 MPa.

When the hydrothermal treatment is performed under the above conditions, flavonoid glycosides can be efficiently decomposed into flavonoids (more specifically, flavonoids and sugars).

(Method for Producing Flavonoids)

A method for producing flavonoids according to the present embodiment includes a decomposition process in which flavonoid glycosides are decomposed and an extraction process in which flavonoids are extracted from a decomposition product obtained in the decomposition process. The decomposition process is a process in which flavonoid glycosides are decomposed by the above method for decomposing flavonoid glycosides according to the present embodiment.

In the extraction process, flavonoids are extracted from a decomposition product obtained in the decomposition process. The decomposition product includes sugars, flavonoid glycosides remaining without decomposition, water-soluble and poorly soluble celluloses and their decomposition products, and the like in addition to the flavonoids. Here, flavonoids are hydrophobic, but sugars, flavonoid glycosides, water-soluble celluloses and their decomposition products are hydrophilic. Therefore, flavonoids are contained in a high concentration in components that are insoluble in the aqueous solution after the hydrothermal treatment, and flavonoids can be concentrated by separating the aqueous solution and insoluble contents after the hydrothermal treatment. In addition, when the water-insoluble content is additionally dissolved in a solvent in which flavonoids are dissolved, for example, ethanol, ethyl acetate, hexane, toluene, or the like, and a mixed solvent thereof, and insoluble components are removed by filtration or the like, it is possible to further extract and purify the flavonoids. Then, flavonoids with a high concentration can be obtained by drying the filtrate.

According to the method, it is possible to efficiently produce flavonoids in a high yield. The flavonoids produced by the production method of the present embodiment may be polymethoxyflavone, sudachitin and/or demethoxysudachitin. The production method of the present embodiment is preferable for producing polymethoxyflavone, particularly, sudachitin and demethoxysudachitin, and the yield thereof can be greatly improved.

EXAMPLES

While the present invention will be described below in more detail with reference to examples and comparative examples, the present invention is not limited to the following examples.

Example 1

2 g of sudachi peel extract powder (commercially available from Ikeda Yakusou Co., Ltd.) containing 1,000 ppm by mass of sudachitin, 1,500 ppm by mass of demethoxysudachitin, 8,000 ppm by mass of glycoside-derived sudachitin, and 3,000 ppm by mass of glycoside-derived demethoxysudachitin was dissolved/dispersed in 50 g of ultrapure water and put into a Teflon (registered trademark) container with a capacity of 100 ml, and additionally, the Teflon (registered trademark) container was placed in a stainless steel pressure-resistant container, and the pressure-resistant container was sealed. In the sealed pressure-resistant container, while stirring the solution in the Teflon (registered trademark) container using a magnetic stirrer at a rotational speed of 600 rpm, heating was performed by a heater so that the temperature of the solution became 180° C. After the temperature reached 180° C., the hydrothermal treatment was performed at 180° C. for 60 minutes while continuing stirring. Then, heating and stirring were stopped and the sample was naturally cooled to room temperature (25° C.). Here, the highest reachable temperature during the hydrothermal treatment was 181° C. After cooling, the solution and solid content in the Teflon (registered trademark) container were taken out with a beaker and vacuum-dried using a diaphragm pump while heating at 60° C. to obtain 1.85 g of a powdered glycoside decomposition sample 1.

Then, again, the same treatment was performed, and after natural cooling after the hydrothermal treatment, the solution and solid content in the Teflon (registered trademark) container were filtered under a reduced pressure using a diaphragm pump using a hydrophilized PTFE membrane filter having an opening of 0.2 µm (commercially available from Merck Millipore, product name: Omnipore 0.2 µm JG). Since decomposed glycoside-derived sugars were dissolved in the separated solution, and the solid component contained the decomposed flavonoids (sudachitin and demethoxysudachitin) in a high concentration, the obtained solid component was put into a 200 cc glass beaker and dried in an oven at 120° C. for 5 hours to obtain a powdered glycoside decomposition product. Then, the glycoside decomposition product was dispersed in ethanol to prepare a 5 mass % dispersion solution and treated under reflux at 60° C. for 1 hour, and flavonoids were extracted in ethanol. Then, the dispersion solution was filtered under a reduced pressure using a hydrophilized PTFE membrane filter having an opening of 0.2 µm (commercially available from Merck Millipore, product name: Omnipore 0.2 µm JG) using a diaphragm pump to obtain a flavonoid lysate. The flavonoid lysate was vacuum-dried using a diaphragm pump while heating at 60° C. to obtain 0.15 g of powdered flavonoid concentrated powder 1.

Examples 2 to 4

Powdered glycoside decomposition samples 2 (1.9 g), 3 (1.81 g), and 4 (1.79 g) and flavonoid concentrated powders 2 (0.15 g), 3 (0.08 g), and 4 (0.05 g) were obtained in the same manner as in Example 1 except that the temperature of the solution during the hydrothermal treatment was set to 160° C. (Example 2), 140° C. (Example 3), and 120° C. (Example 4).

Examples 5 to 8

Powdered glycoside decomposition samples 5 (1.83 g), 6 (1.82 g), 7 (1.75 g), and 8 (1.92 g) and flavonoid concentrated powders 5 (0.16 g), 6 (0.16 g), 7 (0.13 g), and 8 (0.08 g) were obtained in the same manner as in Example 1 except that the reaction time during the hydrothermal treatment was set to 600 minutes (10 hours) and the temperature during the treatment was set to 180° C. (Example 5), 160° C. (Example 6), 140° C. (Example 7), and 120° C. (Example 8).

Examples 9 to 12

Powdered glycoside decomposition samples 9 (4.8 g), 10 (7.3 g), 11 (9.8 g), and 12 (12.2 g) and flavonoid concentrated powders 9 (0.39 g), 10 (0.49 g), 11 (0.41 g), and 12 (0.29 g) were obtained in the same manner as in Example 1 except that 5 g of sudachi peel extract powder (commercially available from Ikeda Yakusou Co., Ltd.) was dissolved/dispersed in 45 g of ultrapure water (Example 9), 7.5 g of sudachi peel extract powder (commercially available from Ikeda Yakusou Co., Ltd.) was dissolved/dispersed in 42.5 g of ultrapure water (Example 10), 10 g of sudachi peel extract powder (commercially available from Ikeda Yakusou Co., Ltd.) was dissolved/dispersed in 40 g of ultrapure water (Example 11), and 12.5 g of sudachi peel extract powder (commercially available from Ikeda Yakusou Co., Ltd.) was dissolved/dispersed in 37.5 g of ultrapure water (Example 12). The sudachi peel extract powder used in Examples 9 to 12 was the same as that used in Example 1.

Example 13

1,330 g of the extraction solvent into which ultrapure water (commercially available from Wako Pure Chemical Industries, Ltd.) and ethanol (special grade, commercially available from Wako Pure Chemical Industries, Ltd.) were mixed at a mass ratio of 6/4 (ultrapure water/ethanol) was put into a 3 L three-necked flask, and while stirring at 320 rpm with a Teflon (registered trademark) stirring blade mounted on a three-one motor (stirrer), when the temperature was adjusted to 60° C. in a hot bath and refluxing was performed in a Liebig cooling pipe, 70 g of dried onion skin powder (commercially available from Shizen Kenkosha Corporation) was added. Stirring was performed for 3 hours, and quercetin and quercetin glycosides contained in the onion skin were extracted.

Then, 60 cc of the above extraction solution was put into a 100 cc plastic container and centrifuging under conditions of 10,000 rpm for 10 minutes was performed in a centrifuge, and the supernatant was taken out with a dropper. Then, 60 cc of a mixed solution containing water/ethanol (mass ratio 6:4) was put into the above plastic container, centrifuging was performed again under the same conditions, and the supernatant was taken out with a dropper. The above operation was performed on the entire extraction solution to obtain 2,540 g of a quercetin and quercetin glycoside extraction solution A. The obtained extraction solution A was dried under a reduced pressure with an evaporator and 11.38 g of the solid content A was obtained. When the concentration of quercetin in the solid content A was analyzed by HPLC, the result was 7.9 mass %.

The same treatment was performed in the same manner as in Example 1 except that the solid content A was used as the raw material and 2 g of the solid content A was used in place of 2 g of sudachi peel extract powder, and 1.91 g of a glycoside decomposition sample 13 and 0.58 g of flavonoid concentrated powder 13 were obtained.

Example 14

0.81 g of a glycoside decomposition sample 14 and 0.32 g of flavonoid concentrated powder 14 were obtained in the same manner as in Example 13 except that the amount of the solid content A was changed to 1 g.

Example 15

0.39 g of a glycoside decomposition sample 15 and 0.31 g of flavonoid concentrated powder 15 were obtained in the same manner as in Example 1 except that 0.5 g of hesperidin (commercially available from Wako Pure Chemical Industries, Ltd., a concentration of 95% or more) as a glycoside of hesperetin, which is one type of flavonoid, was used as the raw material, and this was dissolved/dispersed in 49.5 g of ultrapure water and used as a reaction solution.

Comparative Example 1

2 g of the same sudachi peel extract powder (commercially available from Ikeda Yakusou Co., Ltd.) used in Example 1 was used as a sample of Comparative Example 1.

Reference Example 1

2 g of the same sudachi peel extract powder (commercially available from Ikeda Yakusou Co., Ltd.) used in Example 1 was dissolved/dispersed in 50 g of 1 N hydrochloric acid and heated at 80° C. for 1 hour while stirring at a rotational speed of 600 rpm using a magnetic stirrer, heating and stirring were then stopped and the sample was naturally cooled to room temperature (25° C.). The reaction solution after cooling was neutralized in a 1 N sodium hydroxide aqueous solution and vacuum-dried using a diaphragm pump while heating at 60° C. to obtain 1.74 g of a powdered glycoside hydrochloric acid decomposition sample 1.

Then, the same treatment was performed again, and the reaction solution after natural cooling was neutralized in a 1 N sodium hydroxide aqueous solution, and the solution and solid content were then filtered under a reduced pressure using a hydrophilized PTFE membrane filter having an opening of 0.2 μm (commercially available from Merck Millipore, product name: Omnipore 0.2 μm JG) using a diaphragm pump. Since decomposed glycoside-derived sugars were dissolved in the separated solution, and the solid component contained the decomposed flavonoids (sudachitin and demethoxysudachitin) in a high concentration, the obtained solid component was put into a 200 cc glass beaker and dried in an oven at 120° C. for 5 hours to obtain a powdered glycoside decomposition product. Then, the glycoside decomposition product was dispersed in ethanol to prepare a 5 mass % dispersion solution and treated under reflux at 60° C. for 1 hour, and flavonoids were extracted in ethanol. Then, the dispersion solution was filtered under a reduced pressure using a hydrophilized PTFE membrane filter having an opening of 0.2 μm (commercially available from Merck Millipore, product name: Omnipore 0.2 μm JG) using a diaphragm pump to obtain a flavonoid lysate. The flavonoid lysate was vacuum-dried using a diaphragm pump while heating at 60° C. to obtain 0.15 g of powdered hydrochloric acid decomposed flavonoid concentrated powder 1.

Reference Example 2

The same treatment was performed in the same manner as in Reference Example 1 except that 2 g of the solid content A obtained in Example 13 was used in place of 2 g of the sudachi peel extract powder, and 1.68 g of a powdered glycoside hydrochloric acid decomposition sample 2 and 0.65 g of hydrochloric acid decomposed flavonoid concentrated powder 2 were obtained.

<Evaluation Method>
(Measurement of Flavonoid Concentration in Sample)

The concentrations of the flavonoids of the samples obtained in the examples, comparative examples and reference examples were measured by the following method. First, 0.1 g of the sample was dissolved/dispersed in ethanol so that the dilution factor was 500, and filtered with a PTFE filter having a pore size of 0.1 μm to obtain an ethanol solution. Components of this ethanol solution were analyzed by high performance liquid chromatography (HPLC). Calibration curves were created using a commercially available sudachitin standard purified sample, a commercially available demethoxysudachitin standard purified sample, a quercetin standard purified sample and a hesperetin standard purified sample as standard substances, and used to roughly estimate the concentration of sudachitin, the concentration of demethoxysudachitin, the concentration of quercetin and the concentration of hesperetin in the sample. "Chromaster" (commercially available from Hitachi High-Tech Corporation) was used as the HPLC device. The results are summarized in Table 1 and Table 2.

(Calculation of Yield of Flavonoids)

The ratio of the mass of flavonoids contained in the obtained flavonoid concentrated powder with respect to the mass of flavonoids contained in the raw material powder used in each of the examples and reference examples was determined as a flavonoid yield. The results are shown in Table 1 and Table 2.

TABLE 1

| | Sample | Raw material concentration (mass %) | Hydrothermal treatment temperature (° C.) | Hydrothermal treatment time (hours) | Glycoside decomposition sample | | Flavonoid concentrated powder | |
|---|---|---|---|---|---|---|---|---|
| | | | | | Sudachitin concentration (ppm by mass) | Demethoxysudachitin concentration (ppm by mass) | Sudachitin yield (mass %) | Demethoxysudachitin yield (mass %) |
| Example 1 | Glycoside decomposition sample 1 | 3.8 | 180 | 1 | 8700 | 1600 | 75.1 | 88.1 |
| Example 2 | Glycoside decomposition sample 2 | 3.8 | 160 | 1 | 6400 | 1500 | 70.6 | 84.4 |
| Example 3 | Glycoside decomposition sample 3 | 3.8 | 140 | 1 | 3200 | 1400 | 25.7 | 22.4 |

TABLE 1-continued

| | Sample | Raw material concentration (mass %) | Hydrothermal treatment temperature (° C.) | Hydrothermal treatment time (hours) | Glycoside decomposition sample | | Flavonoid concentrated powder | |
|---|---|---|---|---|---|---|---|---|
| | | | | | Sudachitin concentration (ppm by mass) | Demethoxysudachitin concentration (ppm by mass) | Sudachitin yield (mass %) | Demethoxysudachitin yield (mass %) |
| Example 4 | Glycoside decomposition sample 4 | 3.8 | 120 | 1 | 1500 | 1200 | 5.9 | 5.1 |
| Example 5 | Glycoside decomposition sample 5 | 3.8 | 180 | 10 | 9500 | 1700 | 83.8 | 93.9 |
| Example 6 | Glycoside decomposition sample 6 | 3.8 | 160 | 10 | 8200 | 1600 | 73.3 | 81.3 |
| Example 7 | Glycoside decomposition sample 7 | 3.8 | 140 | 10 | 5400 | 1500 | 52.0 | 69.3 |
| Example 8 | Glycoside decomposition sample 8 | 3.8 | 120 | 10 | 3000 | 1300 | 21.8 | 26.7 |
| Example 9 | Glycoside decomposition sample 9 | 10 | 180 | 1 | 9200 | 1400 | 74.1 | 90.9 |
| Example 10 | Glycoside decomposition sample 10 | 15 | 180 | 1 | 8900 | 1500 | 63.1 | 68.7 |
| Example 11 | Glycoside decomposition sample 11 | 20 | 180 | 1 | 9100 | 1300 | 47.8 | 53.8 |
| Example 12 | Glycoside decomposition sample 12 | 25 | 180 | 1 | 8700 | 1400 | 24.8 | 30.7 |
| Comparative Example 1 | Sudachi peel extract powder | — | — | — | 1000 | 1100 | — | — |
| Reference Example 1 | Glycoside hydrochloric acid decomposition sample 1 | 3.8 | — | — | 9500 | 1700 | 48.7 | 53.3 |

TABLE 2

| | Sample | Raw material concentration (mass %) | Hydrothermal treatment temperature (° C.) | Hydrothermal treatment time (hours) | Glycoside decomposition sample | | Flavonoid concentrated powder | |
|---|---|---|---|---|---|---|---|---|
| | | | | | Quercetin concentration (ppm by mass) | Hesperetin concentration (ppm by mass) | Quercetin yield (mass %) | Hesperetin yield (mass %) |
| Example 13 | Glycoside decomposition sample 13 | 3.8 | 180 | 1 | 79000 | — | 44.0 | — |
| Example 14 | Glycoside decomposition sample 14 | 2 | 180 | 1 | 77000 | — | 86.4 | — |
| Example 15 | Glycoside decomposition sample 15 | 1 | 180 | 1 | — | 560000 | — | 79.7 |
| Reference Example 2 | Glycoside hydrochloric acid decomposition sample 2 | 3.8 | — | — | 120000 | — | 58.0 | — |

As shown in Table 1, it can be understood that, in all of Examples 1 to 12, compared with Comparative Example 1, the concentration of sudachitin and the concentration of demethoxysudachitin increased, and sudachitin glycoside and demethoxysudachitin glycoside were decomposed to newly generate sudachitin and demethoxysudachitin, and the yield of sudachitin and demethoxysudachitin could be improved. In addition, it can be understood that, in Examples 1 to 12, without using hydrochloric acid as in Reference Example 1, the concentration of sudachitin and the concentration of demethoxysudachitin could be improved, and the concentration of sudachitin and the concentration of demethoxysudachitin could be improved to the same extent as if hydrochloric acid had been used depending on conditions. In addition, as shown in Examples 9 to 12, it was confirmed that, when the concentration of the raw material in the reaction solution increased, the concentration of sudachitin and the concentration of demethoxysudachitin in the glycoside decomposition sample did not change greatly, but when the concentration of the raw material was higher, the yield of flavonoids decreased after ethanol extraction and concentration. Here, it was confirmed that, when the concentration of the raw material was 30 mass % or more, undissolved raw materials remained. In addition, as can be clearly understood from the results shown in Table 2, it was confirmed that sufficient quercetin glycoside and hesperidin could be decomposed.

What is claimed is:

1. A method for decomposing flavonoid glycosides, comprising
    performing a hydrothermal treatment on a raw material containing flavonoid glycosides to decompose the flavonoid glycosides into flavonoids,
    wherein the flavonoid glycosides include sudachitin glycoside wherein the raw material is *Citrus sudachi*, and/or demethoxysudachitin glycoside, and
    the hydrothermal treatment is performed under conditions of a temperature of 180° C. to 300° C. for 0.5 to 20 hours.

2. The method for decomposing flavonoid glycosides according to claim 1,
    wherein the hydrothermal treatment is performed in a sealed container containing the raw material.

3. The method for decomposing flavonoid glycosides according to claim 2,
    wherein the hydrothermal treatment is performed by heating a reaction solution containing the raw material and water in the sealed container.

4. The method for decomposing flavonoid glycosides according to claim 3,
    wherein the content of the flavonoid glycosides in the reaction solution with respect to a total amount of the reaction solution is 0.01 to 3 mass %.

5. The method for decomposing flavonoid glycosides according to claim 3,
    wherein the content of an inorganic acid in the reaction solution with respect to a total amount of the reaction solution is 1 mass % or less.

6. The method for decomposing flavonoid glycosides according to claim 2,
    wherein the hydrothermal treatment is performed by supplying water vapor into the sealed container from the outside.

7. The method for decomposing flavonoid glycosides according to claim 1,
    wherein the raw material further contains flavonoids.

8. The method for decomposing flavonoid glycosides according to claim 1, wherein the raw material is a dry powder obtained from the pericarp of *Citrus sudachi*.

9. A method for producing flavonoids, comprising
    a decomposition process in which the flavonoid glycosides are decomposed by the method for decomposing flavonoid glycosides according to claim 1; and
    an extraction process in which flavonoids are extracted from a decomposition product obtained in the decomposition process.

10. The method for decomposing flavonoid glycosides according to claim 1, wherein the hydrothermal treatment is performed under conditions of a temperature of 190° C. to 300° C. for 0.5 to 20 hours.

* * * * *